United States Patent [19]

Van der Knaap

[11] Patent Number: Plant 6,242

[45] Date of Patent: Aug. 2, 1988

[54] CHRYSANTHEMUM PLANT NAMED LILAC BIJOUX

[75] Inventor: Jacques C. M. Van der Knaap, De Lier, Netherlands

[73] Assignee: Fides, Handelskwekerij, De Lier, Netherlands

[21] Appl. No.: 821,537

[22] Filed: Jan. 22, 1986

[51] Int. Cl.[4] ..... A01H 5/00

[52] U.S. Cl. ..... Plt./76

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Lilac Bijoux particularly characterized by its lavender-pink tubular ray floret color; nine week response; spider/anemone capitulum form and excellent flower production.

1 Drawing Sheet

1

The present invention comprises a new and distinct cultivar of Chrysanthemum, botanically known as *Dendranthema morifolium*, Ramat., previously *Chrysanthemum morifolium*, Ramat., and referred to by the cultivar name Lilac Bijoux.

Lilac Bijoux is a product of a planned breeding program which had the objective of creating new chrysanthemum cultivars with spider/anemone capitulum, lavender-pink ray floret color, 9 week response, and the ability to produce commercially acceptable quality in year around cut mum programs. Such traits in combination were not present or needed improvement in previously available commercial cultivars.

Lilac Bijoux was the result of an induced radiation program conducted in De Lier, The Netherlands in 1984. The plants of the parent cultivar Bijoux were subjected to the radiation level of 1750 Krad X-rays.

Lilac Bijoux was discovered and selected as a flowering plant within the group of parent plants by Jacques C. M. Van der Knaap in May of 1984, in a controlled environment in De Lier, The Netherlands.

The first act of asexual reproduction of Lilac Bijoux was accomplished when vegetative cuttings were taken from the initial selection in June of 1984 in a controlled environment in De Lier, The Netherlands by a technician working under formulations established and supervised by Jacques C. M. Van der Knaap. Horticultural examination of selected units initiated Nov. 7, 1984 has demonstrated that the combination of characteristics as herein disclosed for Lilac Bijoux are firmly fixed and are retained through successive generations of asexual reproduction.

Lilac Bijoux has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Lilac Bijoux which, in combination, distinguish this Chrysanthemum as a new and distinct cultivar:

1. Spider/anemone capitulum form.
2. Lavender-pink ray floret color.
3. Nine week response.
4. Excellent flower production per stem.

2

Of the many commercial cultivars known to the present inventor, the most similar in comparison to Lilac Bijoux is Bijoux, disclosed in my pending plant patent application. In comparison to Bijoux, Lilac Bijoux has petals with a larger spoon, more intensive pink flower color and darker green leaves. The disc floret color, capitulum form and capitulum type of Lilac Bijoux are similar to those same characteristics of Bijoux.

The accompanying photographic drawing shows typical inflorescence and foliage characteristics of Lilac Bijoux, with color being as true as reasonably possible in color photographs of this type.

In the following description, color references are made to The Royal Horticultural Society Colour Chart. The color values were determined between 11:00 a.m. and 12:00 noon in May of 1984 under natural day light at De Lier, The Netherlands.

Classification:

*Botanical.*—*Dendranthema morifolium*, Ramat., cv Lilac Bijoux.

*Commercial.*—Cut spider/Anemone spray.

INFLORESCENCE

A. Capitulum:

*Form.*—Anemone.

*Type.*—Spider/anemone.

*Diameter across face.*—70 mm.

B. Corolla of ray florets:

*Color (general tonality from a distance of three meters).*—Pink.

*Color (upper surface).*—RHS 68C (both tubes and spoons).

C. Corolla of disc florets:

*Color (mature).*—Approximately RHS 74D for outer band of disc florets; inner florets are approximately 5A, with slight green tinging.

*Color (immature).*—146C, with darker green in center, maturing to approximately 151A before turning yellow.

D. Reproductive organs:

*Androecium.*—Not present or rudimentary.

*Gynoecium.*—Numerous; present in both disc and ray florets.

PLANT

A. General appearance:

*Height.*—100 cm.

B. Foliage:
*Color* (*upper surface*).—RHS 137B.
*Color* (*under surface*).—RHS 138B.
*Shape.*—Lobed and finely serrated.

I claim:

1. A new and distinct Chrysanthemum plant named

Lilac Bijoux, as described and illustrated, and particularly characterized by its lavender-pink ray floret color; nine week response; spider/anemone capitulum form and excellent flower production.

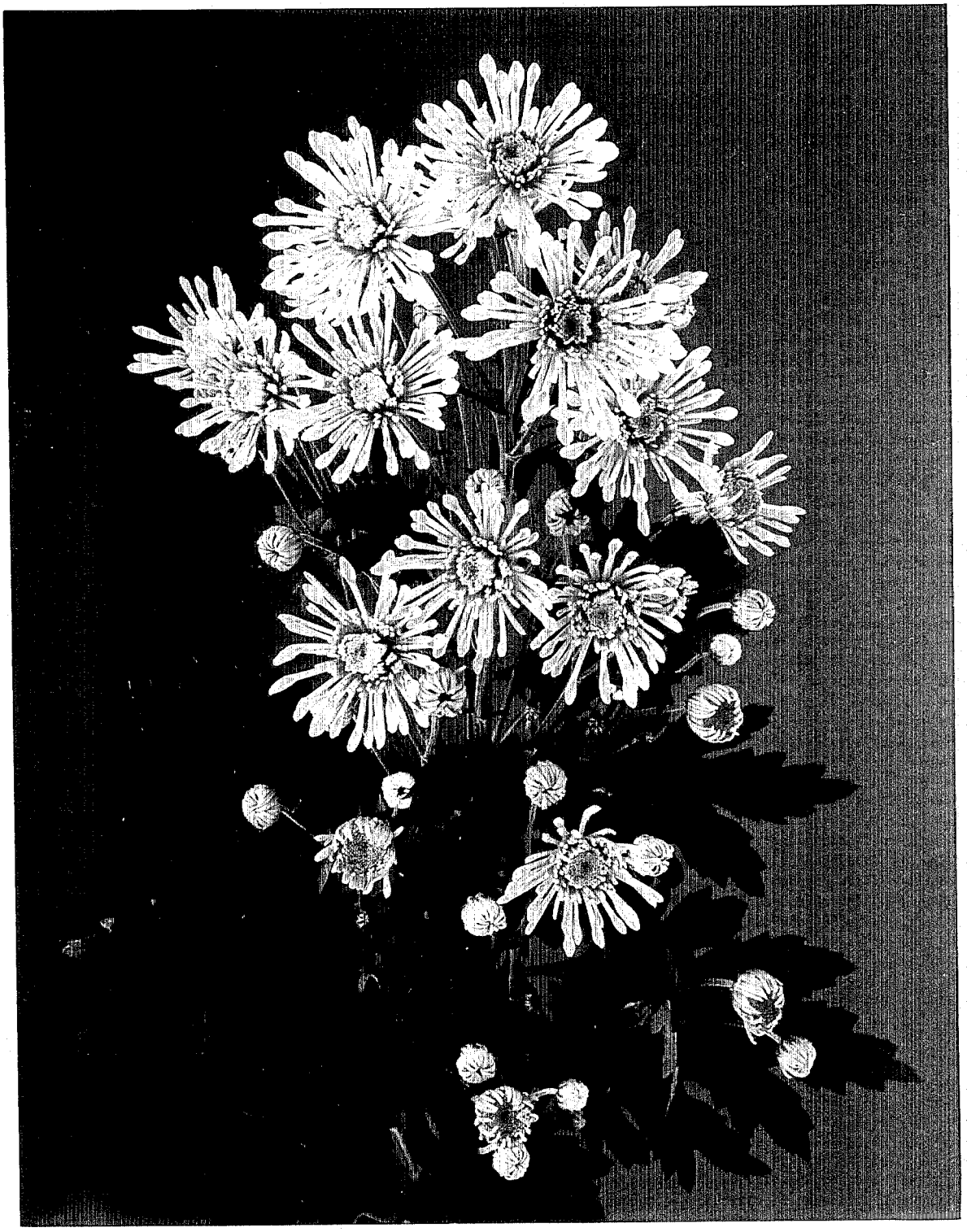

* * * * *